(12) United States Patent
Kidwell et al.

(10) Patent No.: US 6,328,030 B1
(45) Date of Patent: Dec. 11, 2001

(54) NEBULIZER FOR VENTILATION SYSTEM

(76) Inventors: Daniel E. Kidwell, 7841 Rosebush Dr., Indianapolis, IN (US) 46237; Lawrence A. Nilson, 8923 Glass Chimney La., Fishers, IN (US) 46038

( * ) Notice: Subject to any disclaimer, the term of this patent is extended or adjusted under 35 U.S.C. 154(b) by 0 days.

(21) Appl. No.: 09/267,571

(22) Filed: Mar. 12, 1999

(51) Int. Cl.⁷ .................................................. A61M 11/00

(52) U.S. Cl. ............................. 128/200.21; 128/200.14; 128/200.18; 128/200.24; 128/203.16; 128/202.27; 128/205.24; 239/338; 239/505; 239/507

(58) Field of Search ...................... 128/200.14, 200.18, 128/200.21, 200.24, 202.22, 203.16, 202.27, 205.24, 200.22; 239/338, 505, 507, 513, 514, 343, 366

(56) References Cited

U.S. PATENT DOCUMENTS

| | | | |
|---|---|---|---|
| 3,353,536 | * 11/1967 | Bird et al. ............................. | 128/194 |
| 3,826,255 | * 7/1974 | Havstad et al. ....................... | 128/194 |
| 3,903,884 | * 9/1975 | Huston et al. ........................ | 128/194 |
| 3,915,386 | * 10/1975 | Vora ..................................... | 239/338 |
| 3,940,064 | * 2/1976 | Takaoka ................................ | 239/74 |
| 3,968,812 | 7/1976 | Eross . | |
| 4,240,417 | 12/1980 | Holever . | |
| 4,253,468 | * 3/1981 | Lehmbeck ............................ | 128/726 |
| 4,333,450 | * 6/1982 | Lester ................................. | 128/200.14 |
| 4,351,327 | * 9/1982 | Rinne et al. ....................... | 128/200.14 |
| 4,391,271 | 7/1983 | Blanco . | |
| 4,457,305 | 7/1984 | Shanks et al. . | |
| 4,463,755 | * 8/1984 | Suzuki .............................. | 128/204.18 |
| 4,495,946 | * 1/1985 | Lemer ............................... | 128/204.25 |
| 4,560,519 | * 12/1985 | Cerny ................................. | 261/78 A |
| 4,566,480 | * 1/1986 | Parham ............................... | 137/271 |
| 4,653,493 | 3/1987 | Hoppough . | |
| 4,657,007 | 4/1987 | Carlin et al. . | |
| 4,746,067 | 5/1988 | Svoboda . | |
| 4,792,097 | * 12/1988 | Kremer, Jr. et al. ................. | 239/338 |
| 4,805,609 | 2/1989 | Roberts et al. . | |
| 4,823,784 | * 4/1989 | Bordoni et al. ................. | 128/200.14 |

(List continued on next page.)

OTHER PUBLICATIONS

Francie Scott, "Advance for Respiratory Care Practitioners," The Scandal Behind Nosocomial Infections, pp. 6–7, (Dec. 14, 1998).

Acorn II, "Acorn II product information page on website," www.marquestmedical.com.

Primary Examiner—Glenn K. Dawson
Assistant Examiner—Mital Patel
(74) Attorney, Agent, or Firm—Baker & Daniels

(57) ABSTRACT

A nebulizer assembly for engagement in a ventilator circuit is provided in which the nebulizer can be used, maintained and serviced without breaking the ventilation circuit or causing turbulence in the system or loss of pressure. The assembly includes a coupler having two end ports and a lateral port. The coupler defines a chamber in communication with each of the ports. Each of the two end ports are engageable to ventilator circuit hose segments. A tubular housing defines a first opening at a first end and a second opening at an opposite end. The housing defines a passageway between the ends that is in communication with the first opening and the second opening. The first end of the housing is engageable to the lateral port of the coupler. The housing has a bend adjacent the first end of the housing. A valve is disposed within the housing adjacent the first end. The valve has an open position and a closed position and is operable to hermetically seal a portion of the passageway in the chamber in the closed position. A nebulizer defining a lower reservoir for containing liquid and an upper section defining an opening is also provided. The upper section is engageable to the second opening of the housing. The nebulizer includes an atomizer disposed within the reservoir. A medication port that is communicable with the reservoir is provided to deliver liquid medicine to the reservoir. A suction port is also provided for removing residual liquid from the reservoir.

23 Claims, 12 Drawing Sheets

U.S. PATENT DOCUMENTS

| | | |
|---|---|---|
| 4,865,027 | 9/1989 | Laanen et al. . |
| 4,951,661 | 8/1990 | Sladek . |
| 5,054,477 | 10/1991 | Terada et al. . |
| 5,062,419 | 11/1991 | Rider . |
| 5,086,765 * | 2/1992 | Levine ............................ 128/200.21 |
| 5,099,833 * | 3/1992 | Michaels ........................ 128/200.14 |
| 5,119,807 | 6/1992 | Roberts . |
| 5,301,663 | 4/1994 | Small, Jr. . |
| 5,355,872 * | 10/1994 | Riggs et al. .................... 128/200.21 |
| 5,388,571 | 2/1995 | Roberts et al. . |
| 5,425,358 * | 6/1995 | McGrail et al. ............... 128/205.24 |
| 5,479,920 | 1/1996 | Piper et al. . |
| 5,566,669 * | 10/1996 | Konesaroff ..................... 128/205.12 |
| 5,630,409 * | 5/1997 | Bono et al. ..................... 128/200.18 |
| 5,632,298 * | 5/1997 | Artinian ............................... 137/102 |
| 5,653,223 * | 8/1997 | Pruitt ............................... 128/200.21 |
| 5,701,886 | 12/1997 | Ryatt . |
| 5,762,063 | 6/1998 | Coates et al. . |
| 5,813,401 | 9/1998 | Radcliff et al. . |
| 5,823,179 * | 10/1998 | Grychowski et al. .......... 128/200.18 |
| 5,855,203 | 1/1999 | Matter . |
| 5,865,171 * | 2/1999 | Cinquin ........................... 128/203.12 |
| 5,950,623 * | 9/1999 | Michell ........................... 128/205.24 |
| 6,044,841 * | 4/2000 | Verdun et al. .................. 128/200.18 |
| 6,067,984 * | 5/2000 | Piper ................................ 128/205.24 |

* cited by examiner

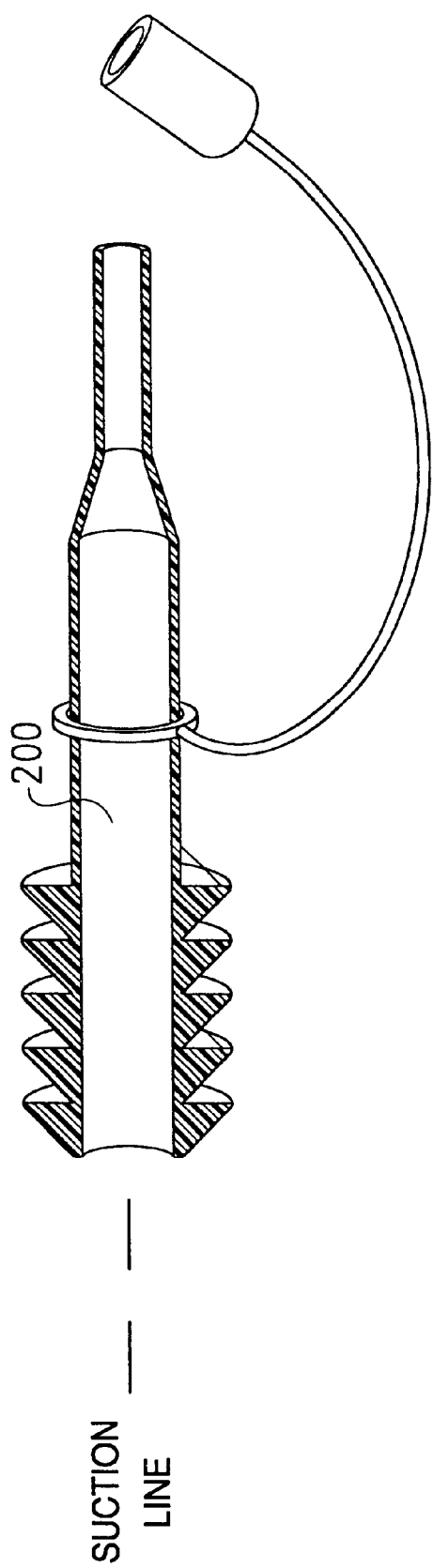

NEBULIZER FOR VENTILATION SYSTEM

FIELD OF THE INVENTION

The present invention relates to pressurized ventilator systems used to supplement a patient's respiration. Specifically, the invention concerns improved nebulizer assemblies for ventilator systems.

BACKGROUND OF THE INVENTION

Patients with respiratory insufficiency often require continuous mechanical ventilation with a positive-pressure ventilator. In such patients a tracheotomy or an endotracheal breathing tube is positioned in the patient's main airway with an internal end positioned for exchange of gas within the lungs and an externally protruding end for connection with a ventilator circuit and then a ventilator system. The ventilator system provides heated, humidified, filtered, breathable gas at a prescribed respiratory rate, tidal volume or pressure, and $FiO_2$ to the patient in repetitive respiration cycles. In each cycle, gas is delivered through the breathing tube into the lungs, and then exhaled gas is permitted to passively flow out of the lungs.

It is frequently necessary or desirable to use a nebulizer to deliver a prescribed amount of liquid medication into the air stream forced through the inspiratory hose of the ventilator circuit. In present practice, to engage the nebulizer to the ventilator circuit, the inspiratory hose is disconnected from the ventilator, a T connector is used to reconnect the inspiratory hose to the ventilator, and a tapered male end of a nebulizer is inserted into the remaining port of the T connector. The nebulizer contains a reservoir for prescribed medications, which are atomized using breathable gas from a separate connection. The medication mist flows from the nebulizer into the inspiratory air stream for the duration of the medication dose. Upon completion of the therapy, the T connector is then removed from the inspiratory side of the circuit. Patients receive medications in this manner from one to twelve times each day.

In order to administer additional nebulizer treatments using existing devices, the practitioner must disassemble the nebulizer in order to add the next medication dose. The residual medication must be emptied from the reservoir and the prescribed dosage introduced. Next the nebulizer is attached to the T connector and placed in the inspiratory side of the ventilator circuit, which requires disconnecting the circuit from the patient. The speed required in safely performing these tasks often results in incomplete removal of condensate, spillage, dropping of the cup-like chamber and consequent delays. Furthermore, if the reservoir is improperly reattached, it results in an ongoing leak in the system. When the nebulizer is removed, the inspiratory hose again is disconnected, the T connector is removed, and inspiratory hose is reconnected to the ventilator.

There are a number of highly undesirable aspects to such methods. Patients who require mechanical ventilation are critically ill. Any disconnection from the machine that they require to sustain their compromised level of health can be life threatening. In fact, some patients are so critically ill that there may be a dramatic deterioration in their vital signs in response to even a momentary break in the ventilator circuit. Moreover, disconnecting certain patients from the positive pressure in the inspiratory hose can cause a partial lung collapse. In addition to the loss of pressure in the system, there is also a risk of contamination and nosocomial infection.

Mucous and condensation frequently build up on the inner walls of the inspiratory hose. Breaking the ventilator circuit exposes hospital personnel to the mucous and possible pathogens. This has become a very important concern with the discovery of the human immunodeficiency virus, the return of certain illnesses, such as tuberculosis, and the widespread development of antibiotic resistant strains of bacteria. In addition to the risk of infection to the health care worker, there is also a risk of cross-contamination as the practitioner moves to other patients. Opening the ventilator circuit also bypasses the defense systems in the patient's upper respiratory system and provides a direct path into the patient's lungs. This often induces a dangerous infection, particularly in patients who are immunocompromised. Moreover, disconnecting the ventilator circuit may cause the endotracheal tube to wobble in the patient's throat, causing considerable discomfort in some cases.

There have been several approaches to addressing some of these issues, some of which are disclosed in U.S. Pat. Nos. 4,805,609, 5,119,807 and 5,388,571 to Roberts and U.S. Pat. No. 4,951,661 to Sladek. These patents disclose nebulizers having connectors for introducing medication from a reservoir into the ventilation circuit. The Roberts patents disclose valve-conduit arrangements to add medication to the nebulizer reservoir and remove residual material so that it is not necessary to open the circuit to service the nebulizer. One limitation of the Roberts devices is that the valves disclosed by Roberts are positioned so that any secretions and condensate from the ventilator circuit could drain into the nebulizer and contaminate it. Another limitation is that the nebulizer remains functionally connected to the ventilator circuit even when it is not in use. As breathable gas passes the mouth of the nebulizer on its way to the patient, some of the air enters the nebulizer instead of traveling to the patient as intended. This can lead to dead space in the circuit as the breathable gas enters the nebulizer reservoir. The only way to functionally close off the Roberts devices from the ventilation circuit is to break the circuit and remove the device, leading to the very problem that Roberts intended to solve.

Sladek discloses a valve that is insertable into the lower opening of a T-shaped connector that is integral with the ventilation circuit. A cap is attached to the valve for closing the lower opening of the valve. When a nebulizer is engaged to the valve through the lower opening of the valve, a valve plate is pushed open to functionally connect the nebulizer to the ventilation circuit. After use, the nebulizer is removed, which closes the valve plate but leaves the lower opening of the valve exposed. The cap can then be placed over the lower opening of the valve to reduce the risk of contamination until the nebulizer is replaced.

The Sladek design requires the practitioners to handle the nebulizer when additional medication is required. This can result in contamination. Also, the short exposure of the valve could result in contamination of the treatment room and the ventilation circuit. Moreover, pushing the valve plate into the air stream causes turbulence and disrupts the air flow to the patient. Several of the Roberts devices also have this disadvantage because components of the assemblies are positioned in the ventilator air path. Therefore none of the known nebulizers disclose means for functionally disconnecting the nebulizer from the ventilator circuit without disconnecting the circuit, exposing the circuit, causing turbulence in the circuit or loss of pressure.

Therefore, a need has remained for ventilator nebulizer assemblies that can be used, maintained and serviced without breaking the ventilation circuit or causing turbulence in the system or loss of pressure.

SUMMARY OF THE INVENTION

Briefly describing one aspect of the invention, a nebulizer assembly for engagement in a ventilator circuit is provided.

The assembly includes a coupler having two end ports, a lateral port and a chamber in communication with each of the ports. Each of the two end ports is engageable to ventilator hose segments. The assembly also includes a tubular housing defining first opening at a first end and a second opening at an opposite second end. The housing defines a passageway between the ends, which is in communication with the first opening and the second opening. The first end of the housing is engageable to the lateral port of the coupler. A valve is disposed within the housing adjacent the first end of the housing. The valve has an open position and a closed position and is operable to hermetically seal a portion of the passageway from the chamber. The assembly further includes a nebulizer, which defines a lower reservoir for containing liquid and an upper section defining an opening. The upper section is engageable to the second opening of the housing. An atomizer is disposed within the reservoir of the nebulizer.

In some embodiments, the valve is arranged to be isolated from the chamber from the coupler when the first end of the tubular housing is engaged to the lateral port of the coupler. In other embodiments, the housing includes a bend adjacent the first end of the housing. In preferred embodiments, the valve is disposed between the lateral port and the bend. The bend forms an angle of between about 85° to about 150°, preferably about 90°.

The valves of this invention include a valve closing portion and a valve opening. The valves also include means for moving the valve member to a position with the valve closing portion blocking the passageway of the housing in the closed position and alternately to a position with the valve opening in communication with the passageway in the open position. In one specific embodiment, the means include a lever, which is operably engaged to the valve, disposed on the outer surface of the housing. In some embodiments, the housing defines a valve seat within the passageway and the valve member has an outer surface corresponding to a contact surface of the valve seat. In one embodiment, the valve member is rounded to correspond with a rounded contact surface of the valve seat.

In a preferred embodiment, the valve includes a flat valve face defining a valve closing portion and a valve opening. The valve preferably includes at least one turning member disposed on an outer perimeter of the valve face, which projects beyond an outer surface of the housing. The turning member is sized and positioned to be manually operable to turn the valve between an open position with the valve opening communicating the passageway with the chamber and a closed position with the valve closing portion blocking the passageway. In a specific embodiment, the housing defines a flange for seating the valve and the valve defines a groove corresponding to the flange for slidingly receiving the flange so that the valve face is rotatable between the open and close positions.

In another specific embodiment, the assembly includes a step up element disposed adjacent the lateral port. The step up element blocks a portion of the lateral port and is adjacent the lateral port to cooperate with the valve closing portion to close the valve. In preferred embodiments, the assembly further includes an outlet tube disposed in the lateral port and extending into the chamber. The outlet tube is in communication with the first opening in the chamber and includes a tubular wall that forms a barrier to fluid in the chamber from entering the first opening.

In preferred embodiments, the assemblies of this invention include a medication port that is communicable with the reservoir for delivering fluid to the reservoir. Preferably the assemblies also include a suction port for removing residual liquid from the reservoir. The suction port includes a suction tube having a first end adjacent a lowest portion of the reservoir and a second end projecting from an outer surface of the nebulizer.

Accordingly, it is one object of the invention to provide improved nebulizer assemblies for mechanical ventilation systems that avoid the need for breaking the ventilation circuit for proper use and maintenance of the assembly. These and other objects, advantages and features are accomplished according to the devices, assemblies and methods of the present invention.

DESCRIPTION OF THE FIGURES

FIG. 17 is a suction line adapter according to this invention.

DESCRIPTION OF THE PREFERRED EMBODIMENTS

Figure 1:
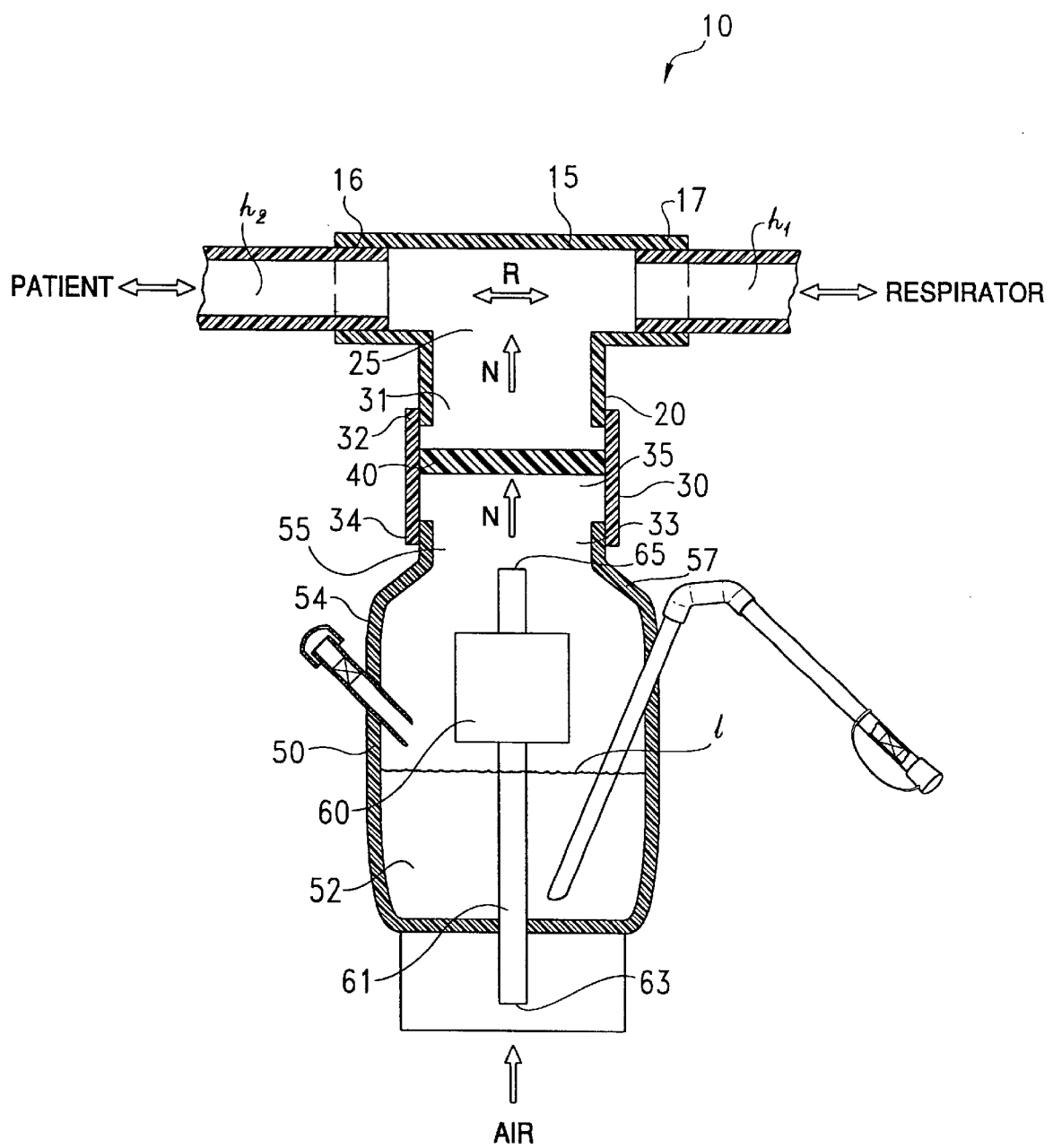
FIG. 1 is a side sectional view of a nebulizer assembly of this invention engaged to a ventilator circuit.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention provides nebulizer assemblies for ventilators that prevent nosocomial infections and contamination of health care workers, as well as complications due to a temporary disruption of pressurization and air flow to the patient.

A nebulizer assembly 10 for engagement in a ventilator circuit in accordance with a preferred embodiment of the invention is depicted in FIG. 1. The assembly 10 includes a coupler 15 having two end ports 16, 17 and a lateral port 20. The coupler 15 defines a chamber 25 that is in communication with each of the ports 16, 17, 20. Chamber 25 forms part of the ventilator circuit when the two end ports 16, 17 are engaged to ventilator hose segments $h_1$ and $h_2$. Ventilator hose segment $h_1$ is connected to a ventilator as is known in the art. Ventilator hose $h_2$ delivers breathable air and atomized medication to the patient.

Assembly 10 also includes a tubular housing 30 defining a first opening 31 at first end 32 and a second opening 33 at an opposite end 34. The housing 30 defines a passageway 35 between the ends 32, 34 and in communication with the first opening 31 and the second opening 33. The first end 32 of the housing is engageable to the lateral port 20 of the coupler 15.

Assembly 10 also includes a nebulizer 50 for nebulizing medications for delivery along the nebulization path (arrow N) and into the ventilator circuit. Nebulizer 50 defines a lower reservoir 52 for containing liquid and an upper section 54 defining an opening 55. The upper section 54 is engageable to the housing 30 with the second opening 33 in communication with the opening 55 of the nebulizer 50. The particular nebulizer 50 that is employed is not critical. Any suitable nebulizer having an atomizer 60 is contemplated. Generally speaking, the nebulizer will include an air intake tube 61 with an air line port 63 for receiving air from an air source and delivering it to the atomizer for discharging atomized medication through the discharge opening 65 and along arrow N.

A valve 40 is disposed within the housing 30 between the first opening 31 and the second opening 33. Any suitable valve is contemplated. Generally, valve 40 has an open position and a closed position and is operable to hermetically seal a portion of the passageway 35 from the chamber 25. Preferably, valve 40 is positioned so that it is isolated from the chamber 25 of the coupler 15 when the first end 32 of the housing 30 is engaged to the lateral port 20. When the dose has been nebulized, valve 40 can be turned to a closed position. Valve 40 allows the nebulizer to be functionally disconnected from the ventilator circuit when it is not in use. When the valve is closed, all of the gas from the respirator and the patient continues along arrow R as if a nebulizer was not in the system. The nebulizer reservoir can then be emptied of any residual material and a new dose of medication can later be added to the reservoir according to the patient's dosing schedule. Because valve 40 does not extend into the chamber 25 at any time, the flow of air along arrow R is never disrupted by the action of the valve 40. This is an improvement over certain prior art devices in which the valve extends into the flow of air between the ventilator and the patient causing turbulence and a disruption in the amount of air delivered to the patient.

The housing, valve and nebulizer assemblies of this invention are also engageable to standard three port couplers such as the coupler 15 depicted in FIG. 1. Alternatively, the present invention also includes coupler-housing devices 75 having integral valves such as the one depicted in FIGS. 2–4. Device 75 includes end port 76, 77 which are engageable to ventilator hose segments similar to those shown in FIG. 1. The coupler-housing device 75 defines a chamber 85 between the two end ports 76, 77. Coupler also includes a lateral port 81 engaged to the ventilator segment 78 of the coupler 75 by a neck portion 79. The neck portion 79 and the lateral port 81 form a tubular housing 80. A passageway 95 is defined through the housing 80 and communicates with the chamber 85 of the ventilator segment 78 at a first end 82 of the housing 80.

Figure 2:
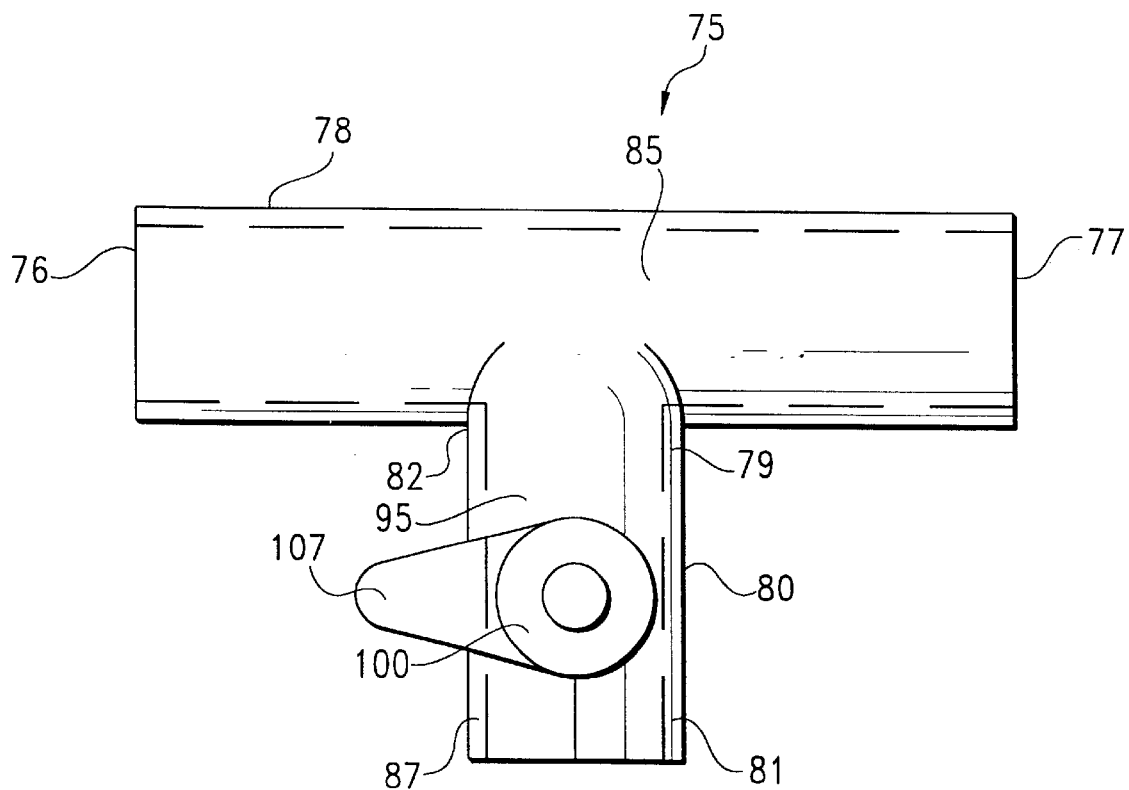
FIG. 2 is a side elevational view of one embodiment of a nebulizer assembly of this invention.
Figure 3:
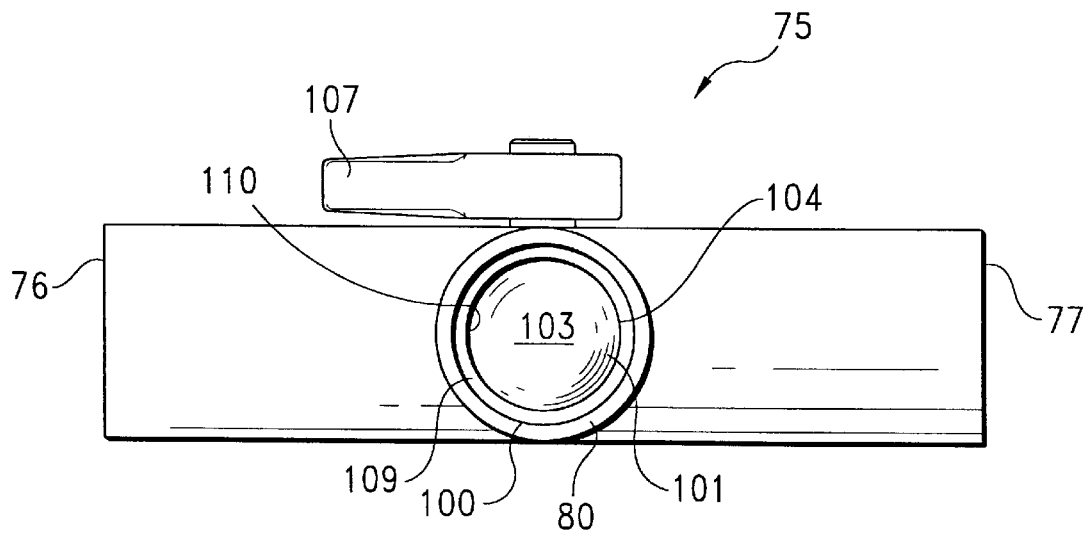
FIG. 3 is the assembly shown in FIG. 2 with the valve in a closed position.
Figure 4:
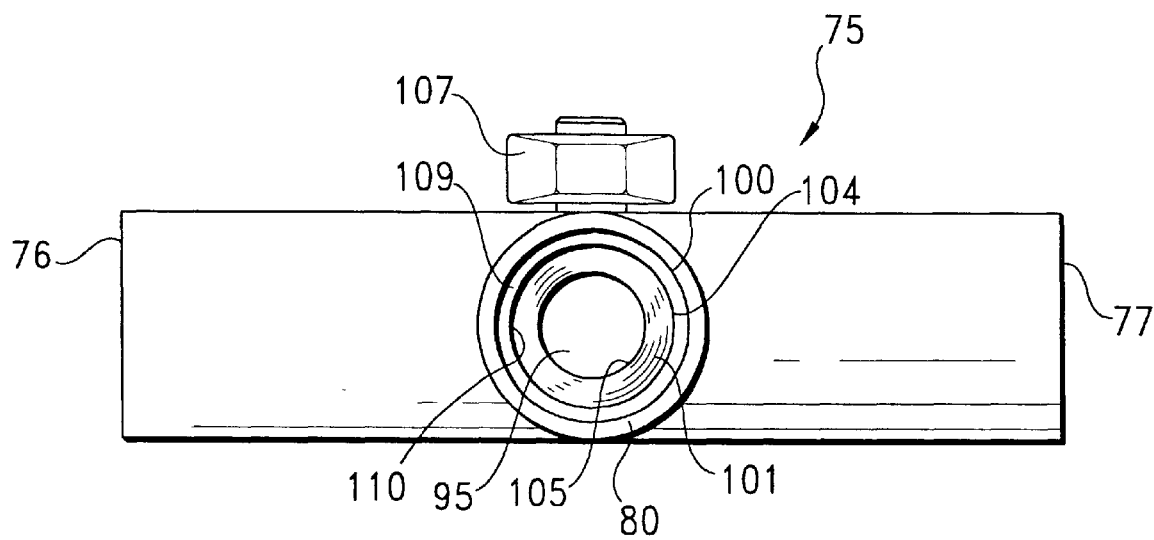
FIG. 4 is a bottom elevational view of the assembly shown in FIG. 2 with the valve in an open position.
Figure 5:
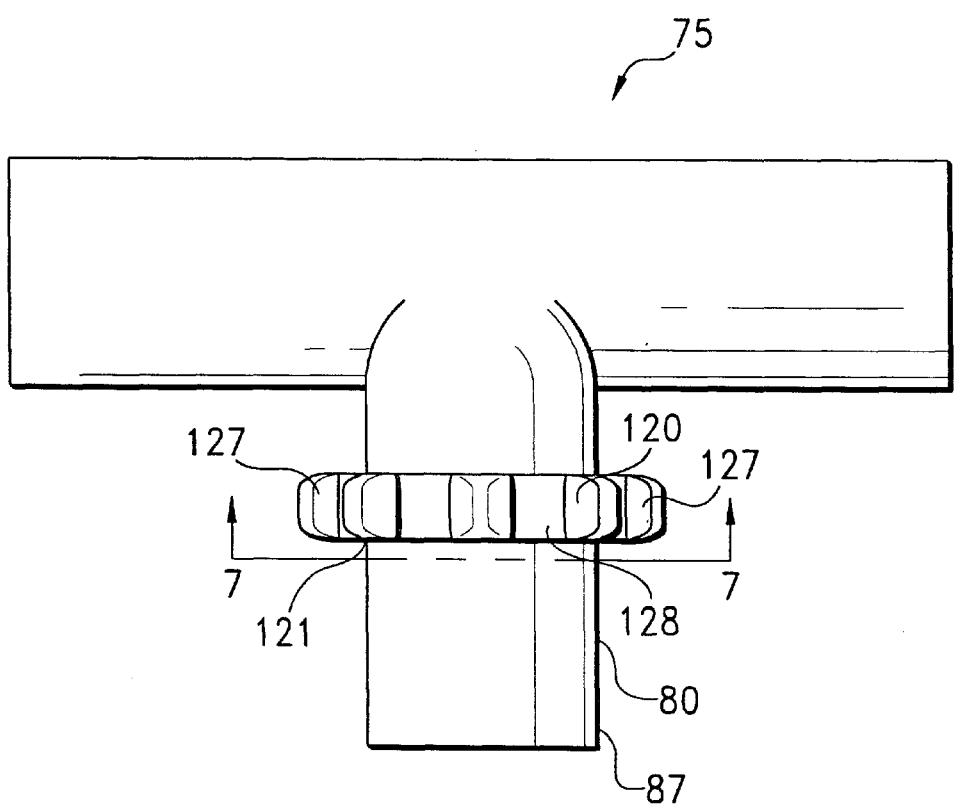
FIG. 5 is a side elevational view of another assembly of this invention.

The assembly includes a valve 100 disposed within the housing 80. Valve 100 preferably includes a valve member 101 and means for actuating the valve member for moving the valve member 101 between an open and a closed position. Valve member 101 includes a valve closing portion 103 and a valve opening 105. In this embodiment, valve member 101 is functionally connected to the means, such as the lever 107, as shown in FIGS. 2–4. Lever 107 is disposed on an outer surface 87 of the coupler 75. The lever 107 is operably engaged to the valve 100 to move the valve member 101 to a closed position with the valve closing portion 103 blocking the passageway 95 as shown in FIG. 3 and alternatively to a position with the valve opening 105 in communication with the passageway 95 in the open position as shown in FIG. 4. In the embodiment depicted in FIGS. 3 and 4, housing 80 defines a valve seat 109 within the passageway 95 and the valve member 101 has an outer surface 104 corresponding to a contact surface 110 of the valve seat 109. In this embodiment, the outer surface 104 is rounded and the contact surface 110 of the valve seat 109 is also rounded to form a ball valve. Valve member 101 is slidably positioned within the valve seat 109 to move the valve member 101 between the open and closed positions.

Figure 6:
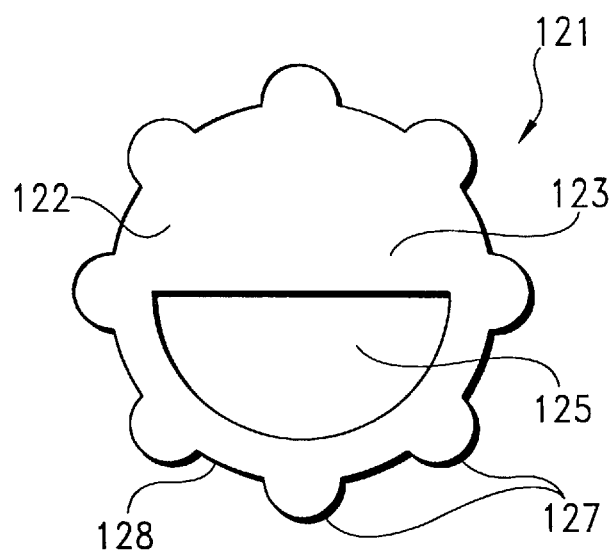
FIG. 6 is a top elevational view of a portion of a valve according to this invention.
Figure 7:
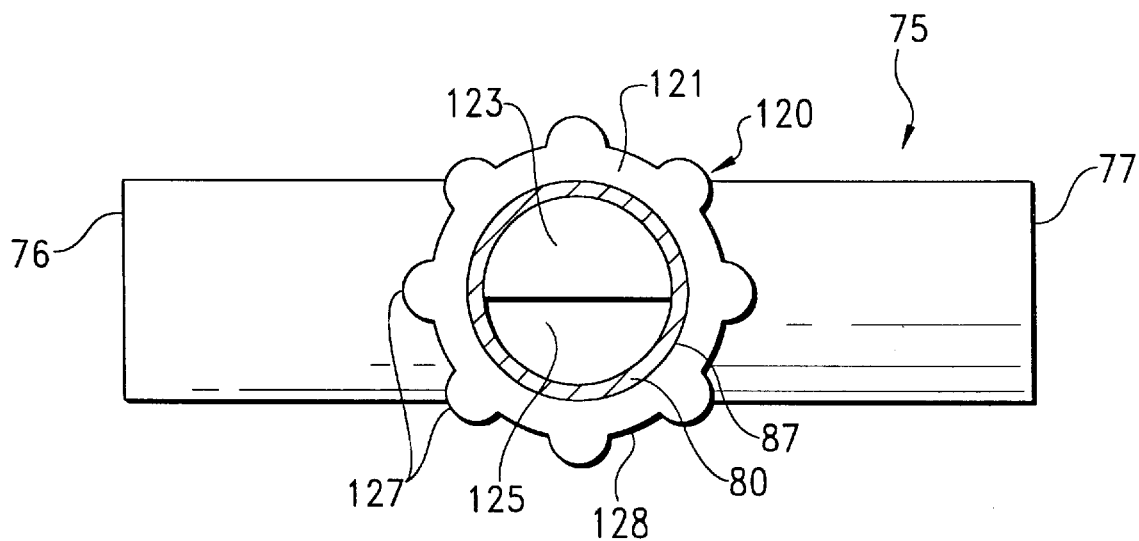
FIG. 7 is a partial cross sectional view shown in FIG. 5 taken along the lines 7—7.
Figure 8:
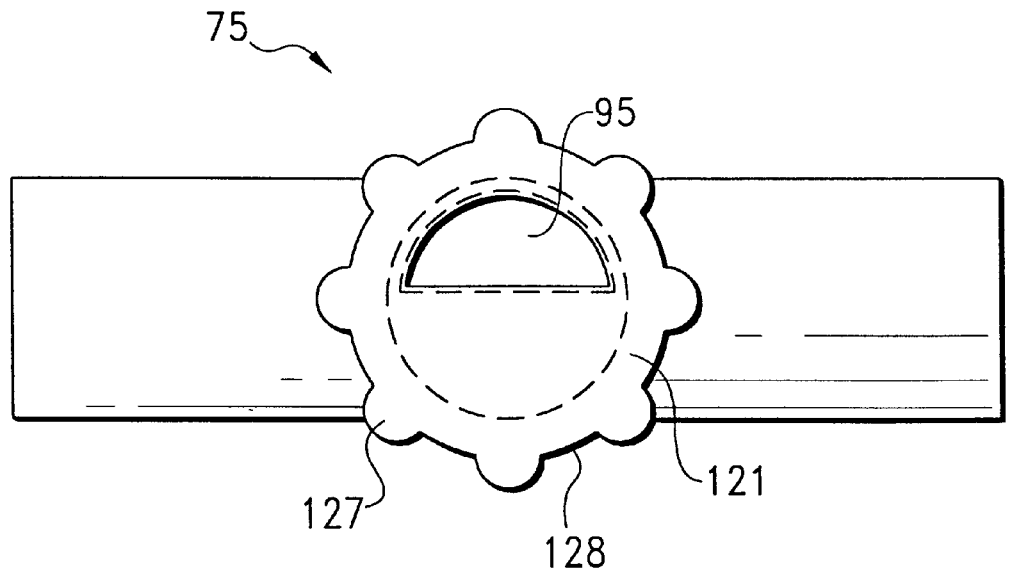
FIG. 8 is a side elevational view of a valve according to one embodiment of this invention engaged to a three-port coupler.
Figure 9:
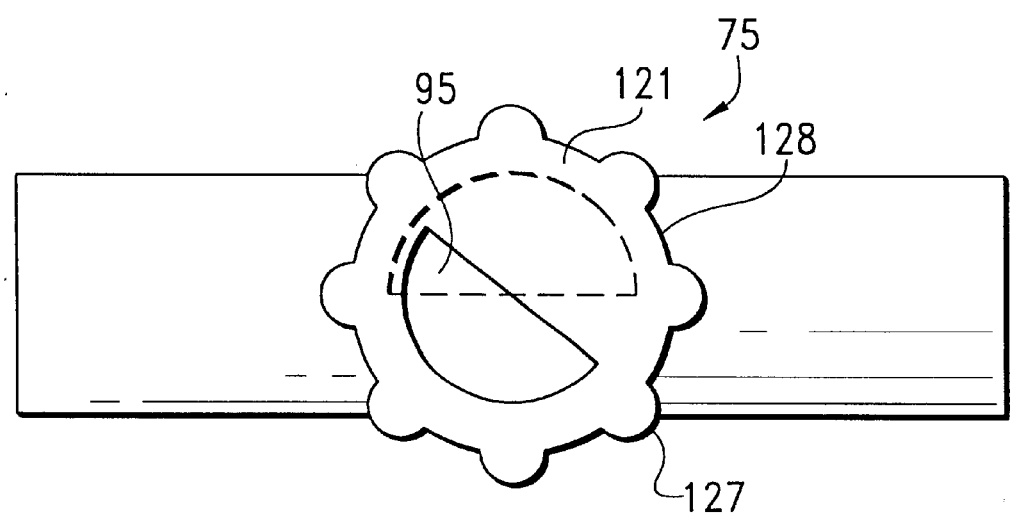
FIG. 9 is a side elevational view of the valve shown in FIG. 8 in a partially closed position.
Figure 10:
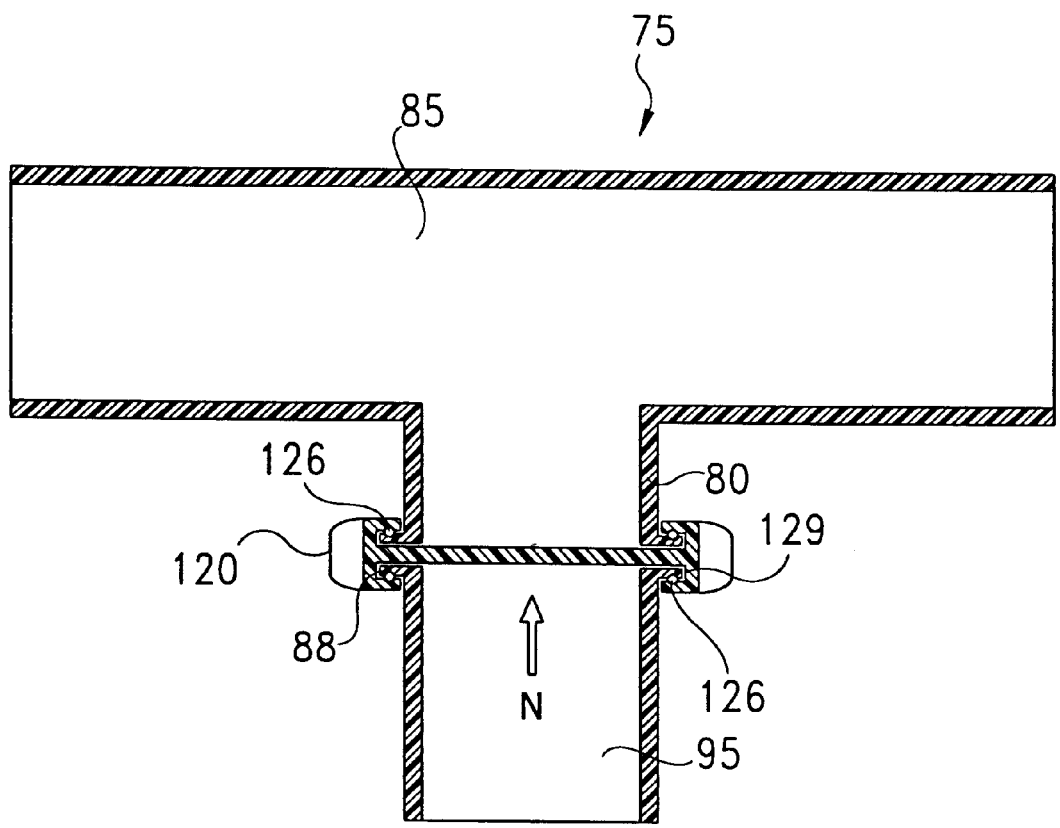
FIG. 10 is a side sectional view of an assembly of this invention.
Figure 11:
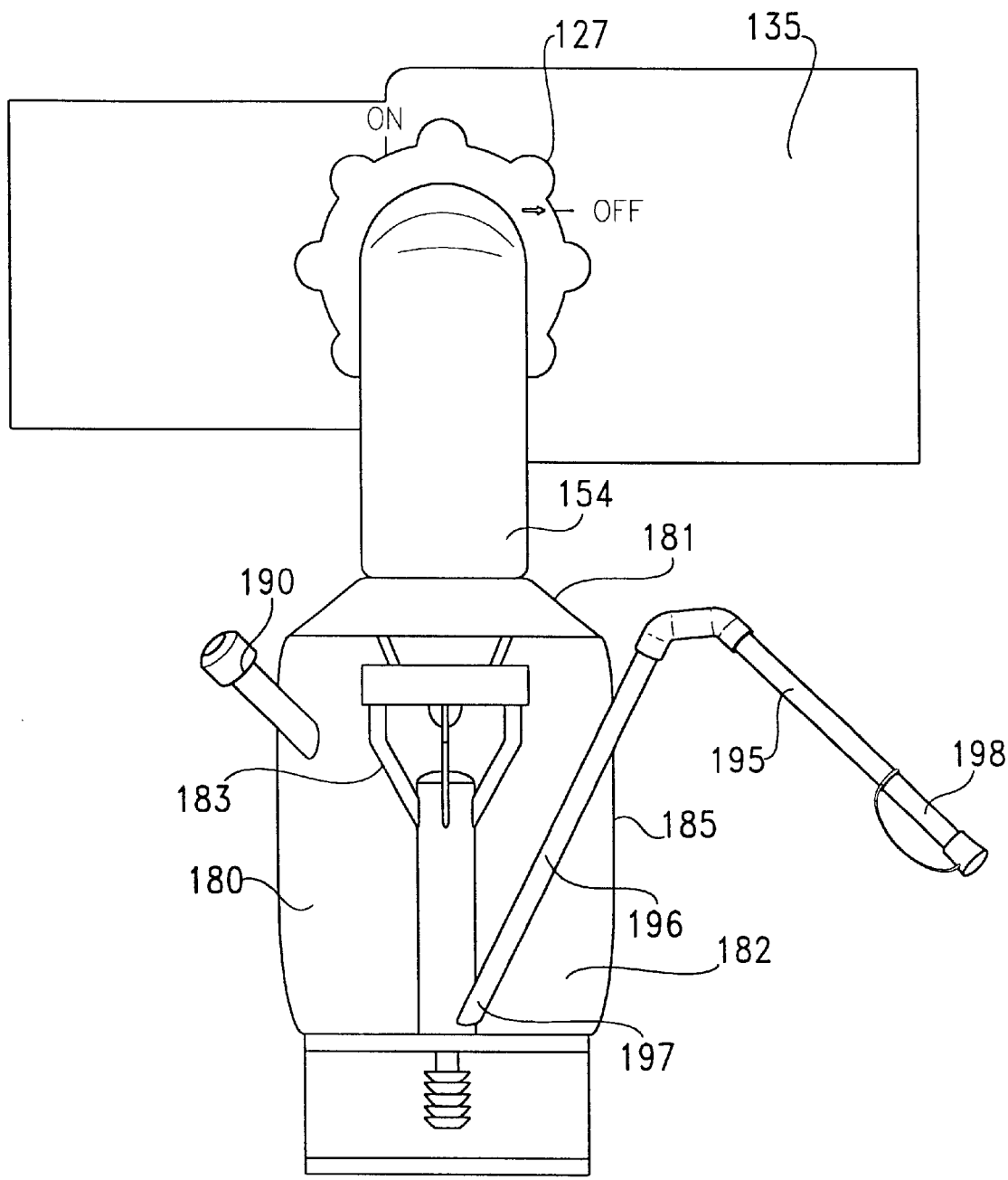
FIG. 11 is a front elevational view of a nebulizer assembly according to one embodiment of this invention.

In another embodiment, depicted in FIGS. 5–10, the coupler-housing device 75 is outfitted with a sliding valve 120. The valve 120 includes a valve member 121 that has a flat valve face 122 as shown in FIG. 6. The valve face 122 defines a valve closing portion 123 and a valve opening 125. The valve member 121 is slidable and rotatable to position the valve face 122 with the valve closing portion 123 locking the passageway 95 in the closed position as shown in FIG. 7 and alternately rotatable to position the valve opening 125 to communicate the passageway with the chamber 85 in the open position as shown in FIG. 8. Preferably, the valve 120 includes a turning member 127 disposed on an outer perimeter 128 of the valve face 122. The turning member 127 projects beyond an outer surface 87 of the housing 80. The turning member 127 is sized to be manually operable to turn the valve 120 between the open and closed position. Preferably, the assembly will be provided with indicia indicating the open and closed positions such as is shown in FIG. 11. The valve 120 may be rotatably and slidingly engaged to the housing in any suitable manner. In the embodiment shown in FIG. 10, the housing 80 defines a flange 88 for seating the valve 120 and the valve 120 defines a groove 129 for slidingly receiving the flange 88. Of course, it is contemplated that the engagement of the flange, and other components of the assemblies of this invention, will include any elements, such as O-ring 126, that are desirable or necessary from a design or manufacturing perspective.

Figure 12:
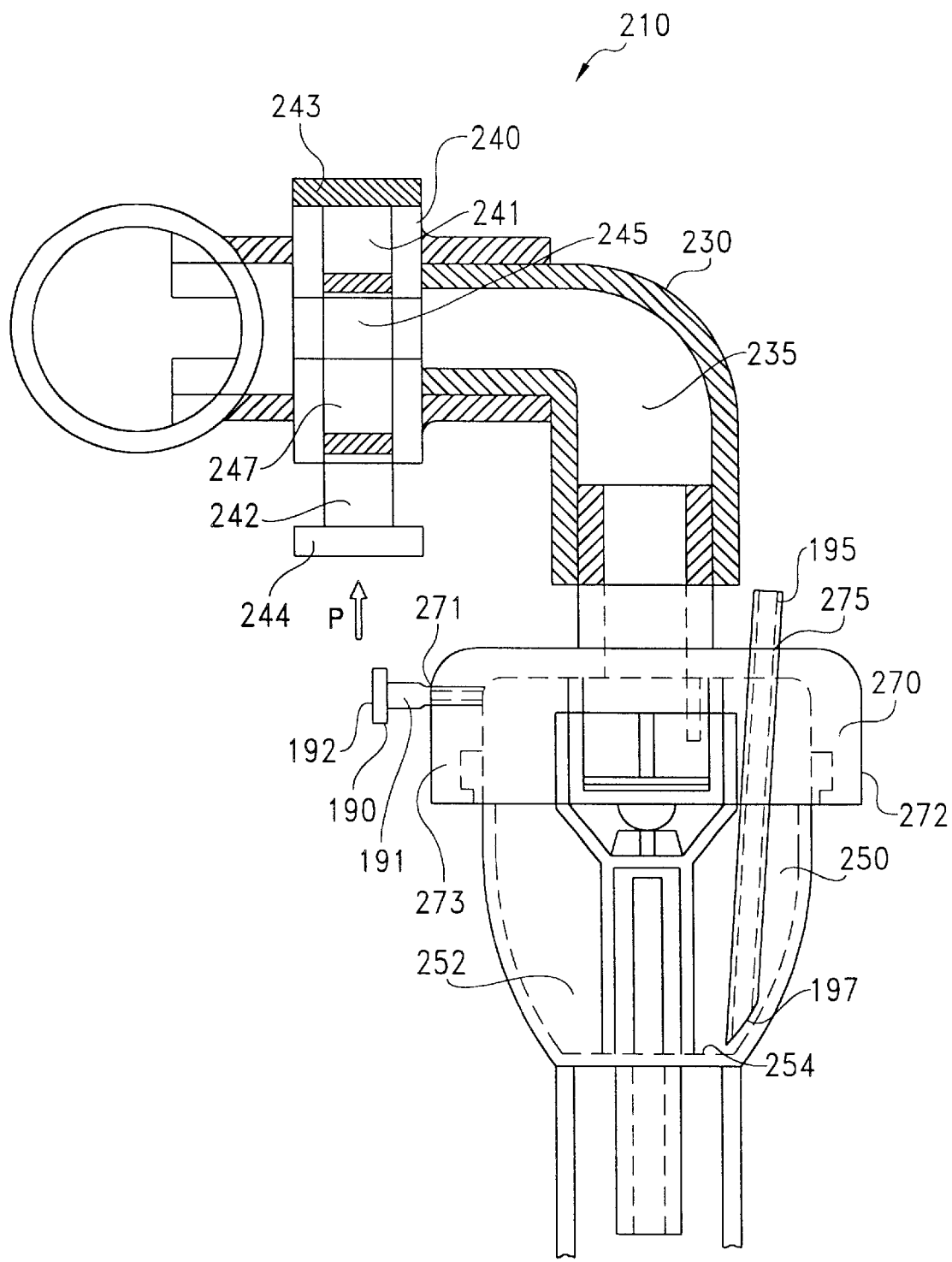
FIG. 12 is a side partial cross sectional view of an assembly according to one embodiment of this invention.

This invention contemplates any suitable valve. For example, a push pull valve 240 is depicted in FIG. 12. The valve 240 includes a pair of actuators 241, 242 that move valve 240 between open and closed positions. In the open position the valve opening 245 is in line with the passageway 235 of the housing 230 as shown in FIG. 12. The actuators 241, 242 can be conveniently operated by manually depressing thumb plates 243, 244, respectively. To move the valve from the open position shown in FIG. 12 to a closed position with the valve closing portion 247 blocking the passageway 235, thumb plate is depressed in the direction of arrow P. To again move the valve to the open position, thumb plate 243 is depressed in the opposite direction.

Figure 13:
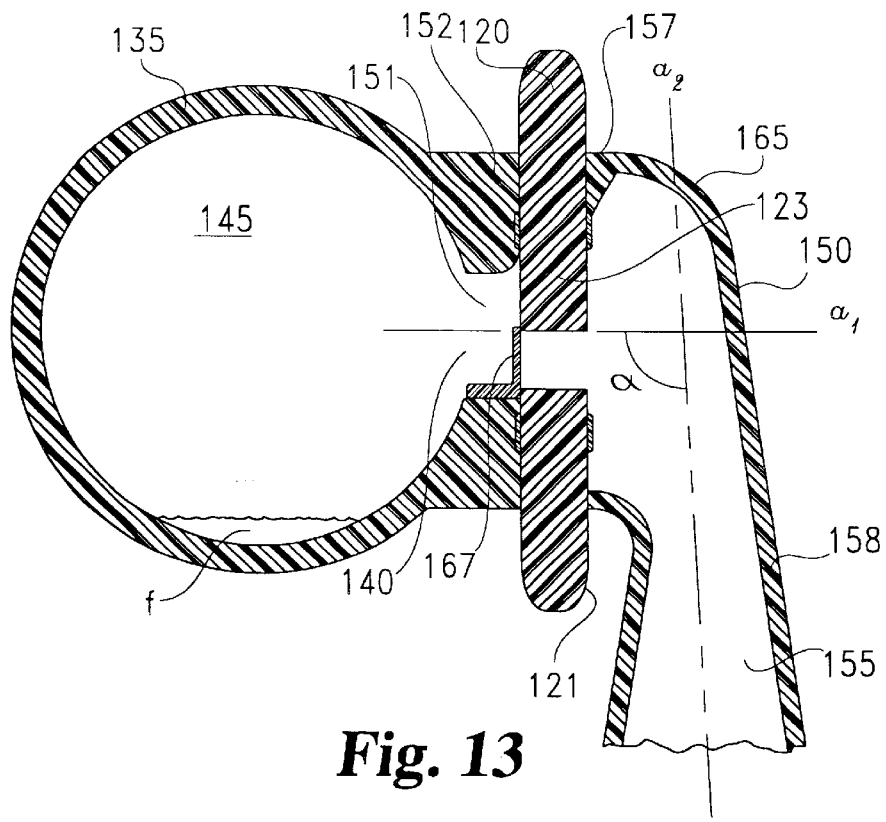
FIG. 13 is a side sectional view of an assembly according to this invention with the valve in a closed position.
Figure 14:
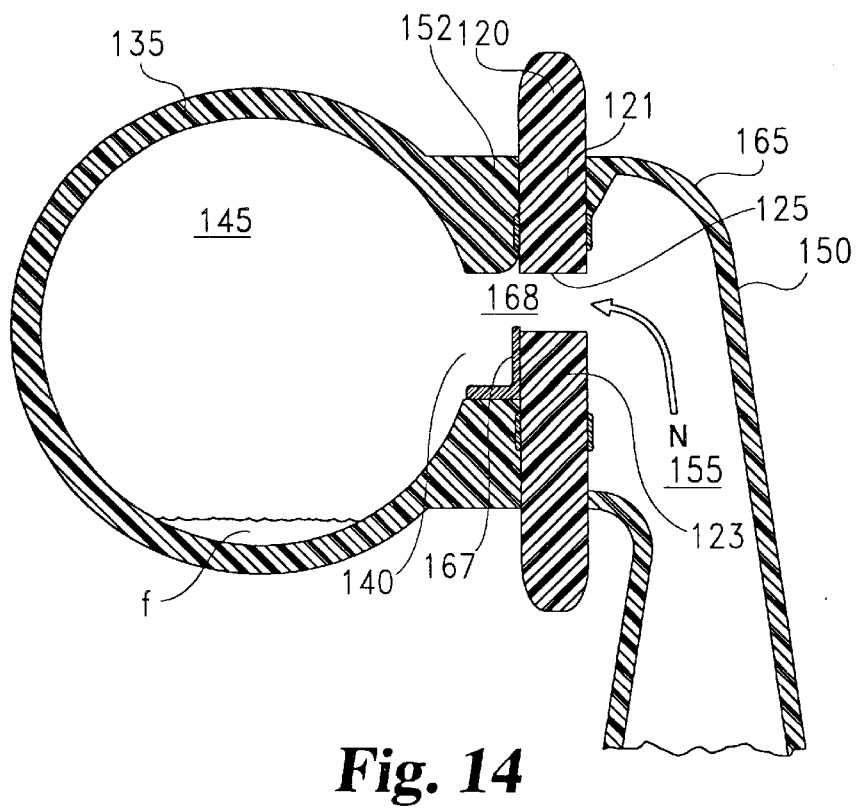
FIG. 14 is a side sectional view of the assembly shown in FIG. 13 with the valve in an open position.
Figure 15:
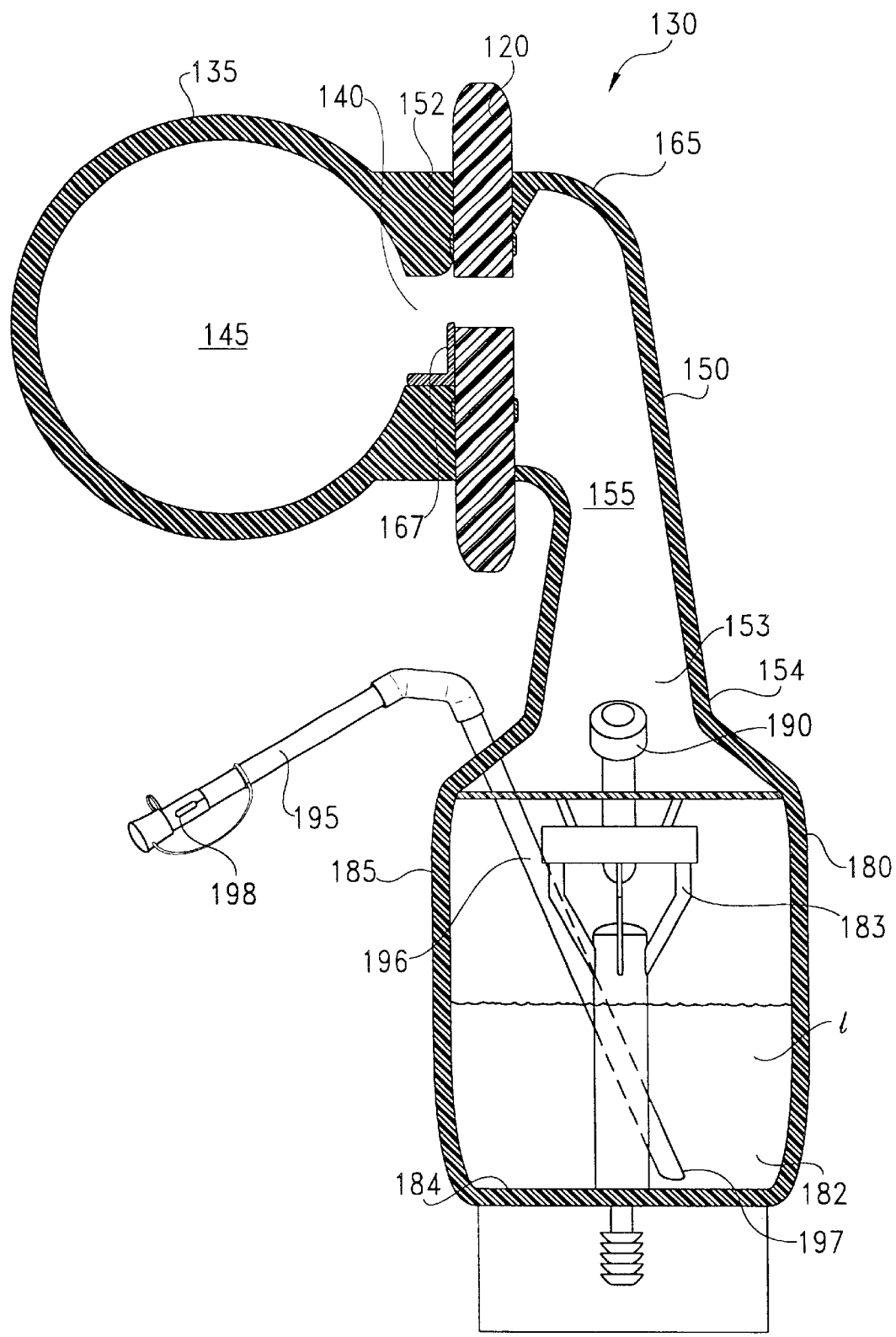
FIG. 15 is a side sectional view of the assembly shown in FIG. 11.

One preferred assembly 130 is depicted in FIGS. 13–15. The assembly 130 includes a coupler 135 for engaging ventilator hose segments as previously discussed. Coupler 135 includes a lateral port 140 and a chamber 145 in communication with the lateral port 140. The assembly further includes a housing 150 having a first opening 151 at a first end 152 of the housing 150 as well as a second opening 153 at a second end 154 of the housing 150. The housing 150 of this embodiment is provided with a bend 165 adjacent the first end 152 of the housing 150. A first portion 157 of the housing 150 adjacent to the first end 152 forms an axis $a_1$. The second portion 158 of the housing 150 forms an axis $a_2$. Preferably the bend 165 orients axis $a_1$ and axis $a_2$ at an angle of between about 85° and 150° and most preferably about 90°. In a most preferred embodiment, sliding valve 120 is disposed between lateral port 140 and bend 165. In this configuration, fluid f from the patient is not drained into passageway 155 as with prior art designs. Moreover, valve 120 does not extend into the chamber 145 at anytime. Thus, valve 120 can be closed to functionally isolate the nebulizer from the circuit without disrupting air flow and pressure for the patient, yet the nebulizer is readily available for re-engagement to the circuit merely by moving the valve to an open position.

In the embodiment shown in FIGS. 13–15, a wall 167 is positioned to block a portion of the passageway 155 to form a smaller dimensioned portion 168 of the passageway 155. Wall 167 is preferably disposed very close to valve 120 between the lateral port 140 and the bend 165. Valve 120 is then rotatable to position valve member 121 with the valve closing portion 123 blocking the smaller dimensioned portion 168 of the passageway 155 in the closed position and alternately rotatable to position the valve opening 125 to communicate the passageway 155 with the chamber 145 in the open position. The wall or step up element 167 further contributes to preventing the passage of fluid f from the patient through the lateral port 140 and into the passageway 155.

Figure 16:
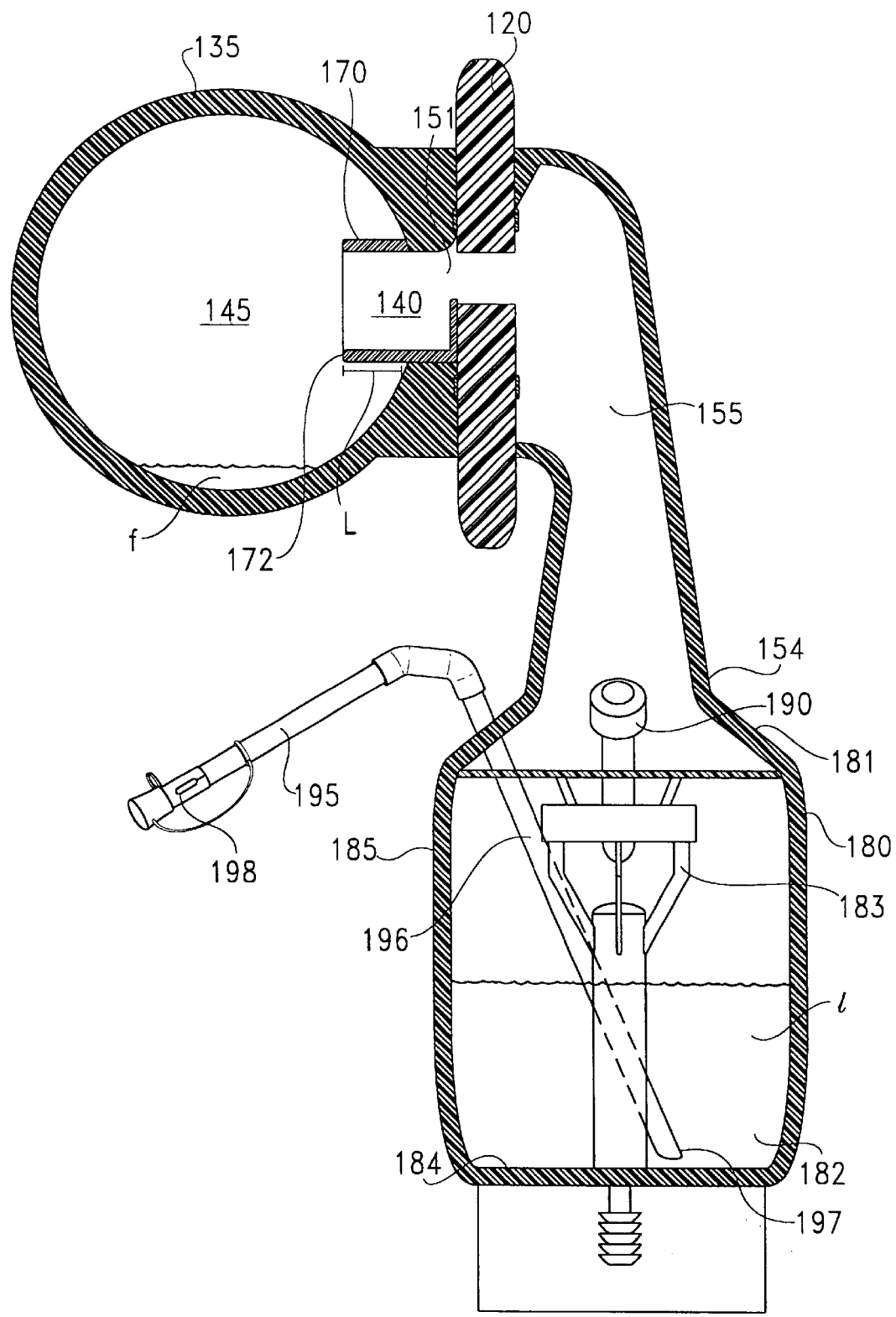
FIG. 16 is a side sectional view of another assembly according to this invention.

To further prevent the backwash of fluid f from chamber 145 into the passageway 155, the assembly depicted in FIG. 16 is further provided to an outlet tube 170. Outlet tube 170 is disposed in the lateral port 140 and extends into the chamber 145. Outlet tube 170 is in communication with the first opening 151 and the chamber 145. Outlet tube 170 includes a tubular wall 172 that has a length L that forms a barrier to fluid in the chamber. Outlet tube 170 will have a length L that is sufficient to form a barrier if the assembly is tilted yet does not extend so far into the chamber 145 so as to cause turbulence in the ventilator circuit. In a preferred embodiment, the length L of the tubular wall 170 was about 3.0 mm.

Any suitable nebulizer is contemplated by this invention and such nebulizers are well known in the art. As shown in FIGS. 11, 15 and 16 the nebulizers 180 can be connected by a reducing diameter shoulder portion 181 to the second end 154 of the housing 150. The shoulder portion is engageable to a standard nebulizer 180, which is available commercially. Alternatively, the nebulizer 180, shoulder portion 181 and housing 150 can be molded into a single piece.

Referring again to FIG. 12, the shoulder portion 270 in one preferred embodiment is a cap like structure that can be attached to a standard nebulizer bowl portion 250. The particular attachment means is not critical to this invention and any suitable means is contemplated. For example, the shoulder 270 may be engaged to the nebulizer 250 with screw-type threads, adhesive, friction fit or any other suitable means, such as integrally molding the pieces 250, 270. The shoulder portion 270 can be engaged to a standard nebulizer portion 250 by the practitioner at the care location. However, it is preferred that the nebulizer portion will be engaged to the rest of the assembly and packaged for use by the practitioner without any assembly required.

The nebulizers of this invention will also preferably include ports for the addition of desired materials and the removal of undesired liquids from the nebulizer reservoir. Referring now to FIGS. 11, 12, 15 and 16, the assemblies include a medication port 190, which allows additional liquid medication l to be added to the nebulizer 180, 250 while the nebulizer assembly is engaged to a ventilator circuit. Nebulizer 180, 250 will also preferably include a suction port 195 for removing residual medication from the reservoir after the particular dose of medication has been dispensed from the nebulizer reservoir 182. Suction port 195 includes a suction tube 196 having a first end 197 adjacent a lowest portion 184 of the reservoir 182. Suction tube 196 also has a second end 198 projecting from an outer surface 185 of the nebulizer 180.

In preferred embodiments, the ports are provided in the shoulder portion 181, 270 as shown in FIGS. 12, 15 and 16. This allows the assemblies of this invention to be fitted to the lower portions of standard nebulizers in an economic and convenient manner. Referring again to FIG. 12, the medication port 190 includes a short inlet tube 191 that extends from an outer surface 272 of the shoulder 270, through an opening 271 defined in the shoulder wall 273 to the reservoir 252 of the nebulizer 250 so that the medication port 190 communicates with the reservoir 252. The medication port preferably includes a flexible piece 192 on an outer end of the port 190 that accepts a syringe. A standard syringe, needleless syringe or similar article punctures the flexible member 192 to deliver medication to the port. The flexible piece 192 is preferably composed of rubber or a similar suitable material. The suction port 195 is also positioned through an opening 275 defined in the shoulder wall 273. The tube 196 is preferably designed to have a length that is compatible with standard nebulizer designs. Preferably, the tube 196 will have a length that allows it to reach the lowest portion 254 of the reservoir 252 when the shoulder 270 is engaged to the nebulizer 250.

After the entire dose of liquid medication has been atomized and received by the patient, the valve is returned to the off or closed position as depicted in FIG. 11. Although the passageway 155 is closed from the chamber 145, the inspiratory stream is not disrupted. Because the valve is isolated from the chamber 145, there is no turbulence from the closing of the valve. With the valve in the closed position, residual medication can be removed through the suction port 195 such as with the suction line adapter 200 depicted in FIG. 17. After the residual fluid is removed from the reservoir 182, a new dose of medication can be added to the reservoir 182 through the medication port 190. The ventilator assemblies of this invention are safe and functional during the entire life of the ventilator circuit.

Preferably, the nebulizer assemblies of this invention will be molded of a single integral piece including the housing and coupler. This is possible because the nebulizer assemblies need never be opened or detached during the entire life of the ventilator circuit. This prevents contamination of the health care worker and infection of the patient as well as any reduction in pressure of the ventilator circuit or disruption of air flow. This invention also reduces the need for special training for quickly and efficiently emptying the reservoirs and prevents accidental detachment of components of the assembly during use or service and maintenance. It is contemplated that in many cases, the assemblies of this invention will be engaged to the ventilator circuit during the initial assembly and set up with the couplers engaged to the ventilator hose segments so that the nebulizer assemblies will be ready for use at any time. Instead of changing and/or detaching the nebulizer with each dose every one to four hours, the nebulizer can be left in place for a week or more for the life of the ventilator circuit. The nebulizer need only be replaced or detached when the ventilator circuit is changed. This will significantly reduce the incidence of ventilator-induced complications.

The present invention shall be more concretely explained with the following example, which are considered to be merely representative of the present invention and thus should not be considered as limiting.

EXAMPLE

A test nebulizer was assembled and inspected for defects or damage. None were found.

The nebulizer was filled with approximately 5 cc of saline to check for leaks. None were found.

The nebulizer was disassembled and dried.

The nebulizer was reassembled and placed inline in the ventilator circuit at patient wye using a standard rubber test lung.

The ventilator was turned on with settings of: Assist control 12, Tidal Volume 800 ml, 0 peep, and 21% $FiO_2$. Appropriate alarm parameters were set for current ventilator settings. The ventilator operated without any alarms.

The nebulizer was reinspected for leaks/defects. None were found.

With the nebulizer in line, a standard leak test was performed to 120 CMH20. Passed without incident.

The ventilator was returned to the previous settings and the medication release valve was opened. Immediately a low volume alarm was encountered. After further inspection, it was noted that the problem was caused from a failure to attach an air source to the air line part of nebulizer. Alarm stopped as soon as the air source was attached.

Exhaled tidal volume was measured at 780 ml prior to installation of the nebulizer.

Exhaled tidal volume was measured at 500 ml after installation of the nebulizer without air source.

Exhaled tidal volume was measured at 770 ml after installation of the nebulizer with air source attached.

The medication release valve was closed. An actual medication treatment was simulated with 3cc of NACL (normal saline) introduced through the medication port with a needless syringe.

The medication release valve was opened and the assembly was observed for leaks. None were found.

The air source was activated and the assembly observed for duration of medication. Noted that approximately 95% of the 3 cc NACL was nebulized as expected.

The medication valve was closed and a suction source was attached at 120 mmhg via a standard suction adapter. All residual NACL was removed in less than three seconds. No alarms or volume loss were detected while suctioning residual medication from nebulizer.

Added approximately 5 cc of NACL to test efficiency of suction port and system design. Again all liquid was removed in approximately 2–3 seconds without problem.

Initial test deemed successful and complete.

The experiments showed that the assemblies of this invention are safe and efficient for administering medication to ventilator patients by nebulization.

The present invention economically and conveniently provides nebulizers for mechanical ventilation systems for patients. With this invention it is not necessary to change the nebulizer for each medication dose. In fact the nebulizer assemblies can be safely and effectively employed for the life of the circuit and need be disconnected from the circuit only when the ventilator circuit is changed in the normal course.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed is:

1. A nebulizer assembly for engagement to a three port coupler of a ventilator circuit hose, the coupler having two end ports and a lateral port and defining a chamber in communication with each of the ports, the assembly comprising:

a tubular housing defining a first opening at a first end and a second opening at an opposite end, said housing defining a passageway between said ends and in communication with said first opening and said second opening, said first end engageable to the lateral port with said first opening in communication with the chamber of the coupler;

a valve disposed within said housing, said valve having an open position and a closed position and operable to hermetically seal a portion of said passageway from the chamber, said valve between said first and second openings and arranged to be isolated from the chamber when said first end is engaged to the lateral port; and a nebulizer defining a lower reservoir for containing liquid and an upper section defining an opening, said upper section engageable to said second opening, said nebulizer including an atomizer disposed within said reservoir.

2. The assembly of claim 1, wherein said valve is a ball valve.

3. The assembly of claim 1, wherein said valve includes a lever disposed on an outer surface of said housing and operably engaged to said valve to move said valve between said closed position and said open position.

4. The assembly of claim 1, wherein said valve includes a valve member defining a valve closing portion and a valve opening, said valve member connected to said lever for moving said valve member to a position with said valve closing portion blocking said passageway in said closed position and alternately to a position with said valve opening in communication with said passageway in said open position.

5. The assembly of claim 4, wherein said housing defines a valve seat within said passageway and valve member has an outer surface corresponding to a contact surface of said valve seat and slidably positioned within said valve seat.

6. The assembly of claim 5, wherein said outer surface of said valve member is rounded and said contact surface of said valve seat is rounded.

7. The assembly of claim 1, wherein said valve includes a flat valve face defining a valve closing portion and a valve opening, said valve rotatable to position said valve face with said valve closing portion blocking said passageway in said closed position and alternately rotatable to position said valve opening to communicate said passageway with said chamber in said open position.

8. The assembly of claim 7, wherein said valve includes a turning member disposed on an outer perimeter of said valve face and projecting beyond an outer surface of said housing, said turning member sized to be manually operable to turn said valve.

9. The assembly of claim 8, wherein said outer surface of said housing defines a flange for seating said valve and said valve defines a groove corresponding to said flange for slidingly receiving said flange.

10. The assembly of claim 1, further comprising:
a medication port communicable with said reservoir for delivering fluid to said reservoir.

11. The assembly of claim 1, further comprising:
a suction port for removing residual liquid from said reservoir, said suction port including a suction tube having a first end adjacent a lowest portion of said reservoir and a second end projecting from an outer surface of said nebulizer.

12. A nebulizer assembly for engagement in a ventilator circuit, comprising:
a coupler having two end ports and a lateral port and defining a chamber in communication with each of said ports, each of said two end ports engageable to ventilator circuit hose segments;
a tubular housing defining a first opening at a first end and a second opening at an opposite end, said housing defining a passageway between said ends and in communication with said first opening and said second opening, said first end engageable to said lateral port, said housing having a bend adjacent said first end of said housing;
a valve disposed within said housing and adjacent said first end of said housing, said valve having an open position and a closed position and operable to hermetically seal a portion of said passageway from said chamber; and
a nebulizer defining a lower reservoir for containing liquid and an upper section defining an opening, said upper section engageable to said second opening of said housing, said nebulizer including an atomizer disposed within said reservoir.

13. The assembly of claim 12, wherein said bend forms an angle of between about 85° and about 150°.

14. The assembly of claim 13, wherein said bend forms an angle of about 90°.

15. The assembly of claim 12 wherein said valve is disposed between said lateral port and said bend.

16. The assembly of claim 15 wherein said valve is disposed between said first and second openings and arranged to be isolated from the chamber when said first end is engaged to said lateral port.

17. The assembly of claim 16, wherein said valve includes a flat valve face defining a valve closing portion and a valve opening, said valve rotatable to position said valve face with said valve closing portion blocking said passageway in said closed position and alternately rotatable to position said valve opening to communicate said passageway with said chamber in said open position.

18. The assembly of claim 17, further comprising:
a step up element disposed adjacent said lateral port, said step up element blocking a portion of said lateral port.

19. The assembly of claim 18, wherein said valve is disposed adjacent to said lateral port and said valve closing portion cooperating with said step up element to close said valve.

20. The assembly of claim 19, wherein said valve includes a turning member disposed on an outer perimeter of said valve face and projecting beyond an outer surface of said housing, said turning member sized to be manually operable to turn said valve.

21. The assembly of claim 19, wherein said outer surface of said housing defines a flange for seating said valve and said valve defines a groove corresponding to said flange for slidingly receiving said flange.

22. The assembly of claim 12, further comprising:
an outlet tube disposed in said lateral port and extending into said chamber, said outlet tube in communication with said first opening and said chamber, said outlet tube having a tubular wall forming a barrier to fluid in said chamber from entering said first opening.

23. The assembly of claim 12, wherein said valve, further comprises:
a wall blocking a portion of said passageway to form a smaller dimensioned portion of said passageway, said wall disposed between said lateral port and said bend; and
a flat valve face defining a valve closing portion and a valve opening, said valve rotatable to position said valve face with said valve closing portion blocking said smaller dimensioned portion of said passageway in said closed position and alternately rotatable to position said valve opening to communicate said passageway with said chamber in said open position.

* * * * *

UNITED STATES PATENT AND TRADEMARK OFFICE
CERTIFICATE OF CORRECTION

PATENT NO.    : 6,328,030 B1  
DATED         : December 11, 2001  
INVENTOR(S)   : Daniel E. Kidwell et al.

Page 1 of 1

It is certified that error appears in the above-identified patent and that said Letters Patent is hereby corrected as shown below:

<u>Column 6,</u>
Line 61, please insert a hyphen in between the words "push" and "pull".

<u>Column 7,</u>
Line 23, please delete the letter "f" in between the words "fluid" and "from" and insert in lieu thereof -- $f$ --.
Line 42, please delete the letter "f" in between the words "fluid" and "from" and insert in lieu thereof -- $f$ --.
Line 45, please delete the letter "f" in between the words "fluid" and "from" and insert in lieu thereof -- $f$ --.

<u>Column 8,</u>
Line 17, please delete the letter "l" in between the words "medication" and "to" and insert in lieu thereof -- $\ell$ --.

<u>Column 10,</u>
Line 58, please delete "1" and insert in lieu thereof -- 3 --.

Signed and Sealed this

Twentieth Day of August, 2002

Attest:

Attesting Officer

JAMES E. ROGAN  
*Director of the United States Patent and Trademark Office*